(12) United States Patent
Chavali et al.

(10) Patent No.: US 11,728,010 B2
(45) Date of Patent: *Aug. 15, 2023

(54) METHODS AND SYSTEMS FOR IDENTIFYING PROGENIES FOR USE IN PLANT BREEDING

(71) Applicant: MONSANTO TECHNOLOGY LLC, St. Louis, MO (US)

(72) Inventors: Srinivas Phani Kumar Chavali, St. Louis, MO (US); Sambarta Dasgupta, St. Louis, MO (US); Mahdi Jadaliha, Chesterfield, MO (US); Anthony Paul Kovacs, Creve Coeur, MO (US); Nalini Polavarapu, St. Louis, MO (US); Zi Wang, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1286 days.

This patent is subject to a terminal disclaimer.

(21) Appl. No.: 16/213,596

(22) Filed: Dec. 7, 2018

(65) Prior Publication Data

US 2019/0180845 A1 Jun. 13, 2019

Related U.S. Application Data

(60) Provisional application No. 62/596,905, filed on Dec. 10, 2017.

(51) Int. Cl.
| | |
|---|---|
| *G16B 40/00* | (2019.01) |
| *A01H 1/02* | (2006.01) |
| *G16B 20/00* | (2019.01) |
| *G16B 10/00* | (2019.01) |
| *A01H 1/04* | (2006.01) |

(52) U.S. Cl.
CPC .............. *G16B 40/00* (2019.02); *A01H 1/02* (2013.01); *A01H 1/04* (2013.01); *G16B 10/00* (2019.02); *G16B 20/00* (2019.02)

(58) Field of Classification Search
None
See application file for complete search history.

(56) References Cited

U.S. PATENT DOCUMENTS

| | | |
|---|---|---|
| 6,285,999 B1 | 9/2001 | Page |
| 7,269,587 B1 | 9/2007 | Page |
| 9,727,639 B2 | 8/2017 | Groeneveld et al. |
| 9,727,926 B2 | 8/2017 | Napper et al. |
| 9,734,239 B2 | 8/2017 | Allen et al. |
| 10,327,400 B2 | 6/2019 | Chavali et al. |
| 2005/0144664 A1 | 6/2005 | Smith et al. |
| 2007/0083456 A1 | 4/2007 | Akers |
| 2010/0100980 A1 | 4/2010 | Bull et al. |
| 2011/0179020 A1 | 7/2011 | Ozzie et al. |
| 2011/0224911 A1 | 9/2011 | Ostrander et al. |
| 2013/0117878 A1 | 5/2013 | Bink et al. |
| 2013/0340110 A1 | 12/2013 | Robbins et al. |
| 2014/0130200 A1 | 5/2014 | Bliss |
| 2015/0080238 A1 | 3/2015 | Ragot et al. |
| 2017/0156276 A1 | 6/2017 | Bull et al. |
| 2017/0223947 A1 | 8/2017 | Gall et al. |
| 2017/0295735 A1 | 10/2017 | Butruille et al. |
| 2017/0354105 A1 | 12/2017 | Polavarapu et al. |
| 2019/0174691 A1 | 6/2019 | Chavali et al. |
| 2019/0313591 A1 | 10/2019 | Chavali et al. |

FOREIGN PATENT DOCUMENTS

| | | |
|---|---|---|
| WO | WO 2013/026085 A1 | 2/2013 |
| WO | WO 2016/022517 A1 | 2/2016 |
| WO | WO 2016/025848 A1 | 2/2016 |
| WO | WO 2017/214445 A1 | 12/2017 |

OTHER PUBLICATIONS

Faux, Anne-Michelle et al., "AlphaSim: Software for Breeding Program Simulation", The Plant Genome, vol. 9, No. 2, Nov. 2016 (published Sep. 22, 2016), pp. 1-14.

Lado, Bettina et al., "Strategies for Selectin Crosses Using Genomic Prediction in Two Wheat Breeding Programs", The Plant Genome, vol. 10, No. 2, Jul. 2017 (publushed Jul. 13, 2017), pp. 1-13.

Charcosset, A. et al., "Prediction of Maize Hybrid Silage Performance Using Marker Data: Comparison of Several Models for Specific Combining Ability", Crop Science, vol. 38, No. 1, Jan. 1998, pp. 38-44.

Xu, S. et al., "Predicting hybrid performance in rice using genomic best linear unbiased prediction", Proceedings of the NAtional Academy of Sciences, vol. 111, No. 34, Aug. 2014, pp. 12456-12461.

Akdemir, Deniz, and Julio I. Sánchez. "Efficient breeding by genomic mating."*Frontiers in genetics* 7 (2016), 11 pages.

Bishop, Christopher M., Pattern recognition and machine learning, Springer (2006) 758 pages.

Bollobás, Béla, Graduate Texts in Mathematics, *Modern graph theory*. vol. 184. Springer Science & Business Media, 2013, 409 pages.

(Continued)

*Primary Examiner* — G Steven Vanni

(74) *Attorney, Agent, or Firm* — Harness, Dickey & Pierce, P.L.C.

(57) ABSTRACT

Exemplary methods for identifying progenies for use in plant breeding are disclosed. One exemplary computer-implemented method includes accessing a data structure including data representative of a pool of progenies and determining a prediction score for at least a portion of the pool of progenies based on the data included in the data structure. The prediction score indicates a probability of selection of the progeny based on historical data. The method further includes selecting a group of progenies from the pool of progenies based on the prediction score, identifying a set of progenies, from the group of progenies, based on at least one of an expected performance of the group of progenies and at least one factor associated with the set of progenies, the pool of progenies and/or the group of progenies, and directing the set of progenies into a validation phase of a breeding pipeline.

18 Claims, 5 Drawing Sheets

(56) References Cited

OTHER PUBLICATIONS

Ensemble Methods in Data Mining: Improving Accuracy Through Combining Predictions, Giovanni Seni and John Elder, 2010 (Morgan and Claypool Publishers), 126 pages.
Ensemble-based classifiers, Rokach (2010), *Artificial Intelligence Review* 33 (1-2): 1-39.
Fernández-Madrigal, J-A., and Javier González. "Multihierarchical graph search." *IEEE Transaction on Pattern Analysis and Machine Intelligence*24.1 (2002): 103-113.
Fortunato, Santo. "Community detection in graphs." *Physics reports* 486.3 (2010): 75-174.
Greg Linden, Brent Smith and Jeremy York. Amazon.com recommendations: Item-to-item collaborative filtering. IEEE Internet Computing, 7(1): 76-80, 2003.
Han, Ye, et al. "The Predicted Cross Value for Genetic Introgression of Multiple alleles." *Genetics* 205.4 (2017): 1409-1423.
Isidro, Julio, et al. "Training set optimization under population structure in genomic selection." *Theoretical and applied genetics* 128.1 (2015): 145-158.
Jure Leskovec, Lada A. Adamic, and Bernardo A. Huberman. The dynamcis of viral marketing. ACM Transactions on the web (ACMTWEB), 1(1), 2007, 39 pages.
Lars Backstrom and Jure Leskovec. Supervised random walks: Prediction and recommending links in social networks. Proceedings of WSDM 2011, pp. 635-644, 2011.
Li, Xin, and Hsinchun Chen. "Recommendation as link prediction in bipartite graphs: A graph kernel-based machine learning approach." Decision Support Systems 54.2 (2013): 880-890.
Mirza, Batul J., Benjamin J. Keller, and Naren Ramakrishnan. "Studying recommendation algorithms by graph analysis." Journal of Intelligent Informantion Systems 20.2 (2003): 131-160.
Murphy, Kevin P., Machine learning: a probabilistic perspective (MIT press, 2012), 1105 pages.
Popular ensemble methods: An empirical study, Opitz & Maclin (1999), *Journal of Artificial Intelligence Research* 11: 169-98.
Stanford large network dataset collection. http://snap.stanford.edu/data/index.html, accessed Nov. 2017, 5 pages.
Thulasiraman, Krishnaiyan, and Madisetti NS Swamy. *Graphs: theory and algorithms*. John Wiley & Sons, 2011, 470 pages.
Wasserman, Stanley, and Katherine Faust. *Social network analysis: Methods and applications*. vol. 8. Cambridge university press (1994), 116 pages.
Zhou, Tao, et al. "Bipartite network projection and personal recommendation." Physical Review E 76.4 (2007): 046115.
Ivandro Bertan et al., Parental Selection Strategies in Plant Breeding Programs, Journal of Crop Science and Biotechnology, vol. 10, No. 4, Jan. 1, 2007, pp. 211-222.
Sun X et al., The role and basics of computer simulation in support of critical decisions in plant breeding, Molecular Breeding, Kluwer Academic Publishers, vol. 28, No. 4, Sep. 10, 2011, pp. 421-436.
Jannink et al., Genomic selection in plant breeding: from theory to practice, Briefings in Functional Genomics, vol. 9, No. 2, Feb. 15, 2010, pp. 166-177.

US 11,728,010 B2

METHODS AND SYSTEMS FOR IDENTIFYING PROGENIES FOR USE IN PLANT BREEDING

CROSS-REFERENCE TO RELATED APPLICATION

This application claims the benefit of and priority to U.S. Provisional Application No. 62/596,905, filed on Dec. 10, 2017. The entire disclosure of the above application is incorporated herein by reference.

FIELD

The present disclosure generally relates to methods and systems for use in plant breeding, and in particular to methods and systems for identifying a set of progenies, from a pool of potential progenies, based on prediction frameworks and/or optimization frameworks, and populating a breeding pipeline with the identified set of progenies.

BACKGROUND

This section provides background information related to the present disclosure which is not necessarily prior art.

In plant development, modifications are made in the plants, either through selective breeding or genetic manipulation. When a desirable improvement is achieved, a commercial quantity is developed by planting seeds from selected ones of the plants and harvesting resulting seeds over several generations. Throughout the process, numerous decisions are made based on characteristics and/or traits of the plants being bred, and similarly on characteristics and/or traits of progeny, which are not guaranteed to inherit or exhibit the desired traits of parents and/or ancestors of the progeny. Traditionally, as part of selecting particular plants for further development, samples are taken from the plants and/or their resulting seeds and tested so that plants having the desired characteristics and/or traits are advanced. In connection therewith, plant development involves large numbers of possible crosses, resulting in large numbers of potential progeny, from which final breeding decisions must be made and/or commercial products must be selected.

DRAWINGS

The drawings described herein are for illustrative purposes only of selected embodiments, are not all possible implementations, and are not intended to limit the scope of the present disclosure.

Corresponding reference numerals indicate corresponding parts throughout the several views of the drawings.

DETAILED DESCRIPTION

Figure 1:
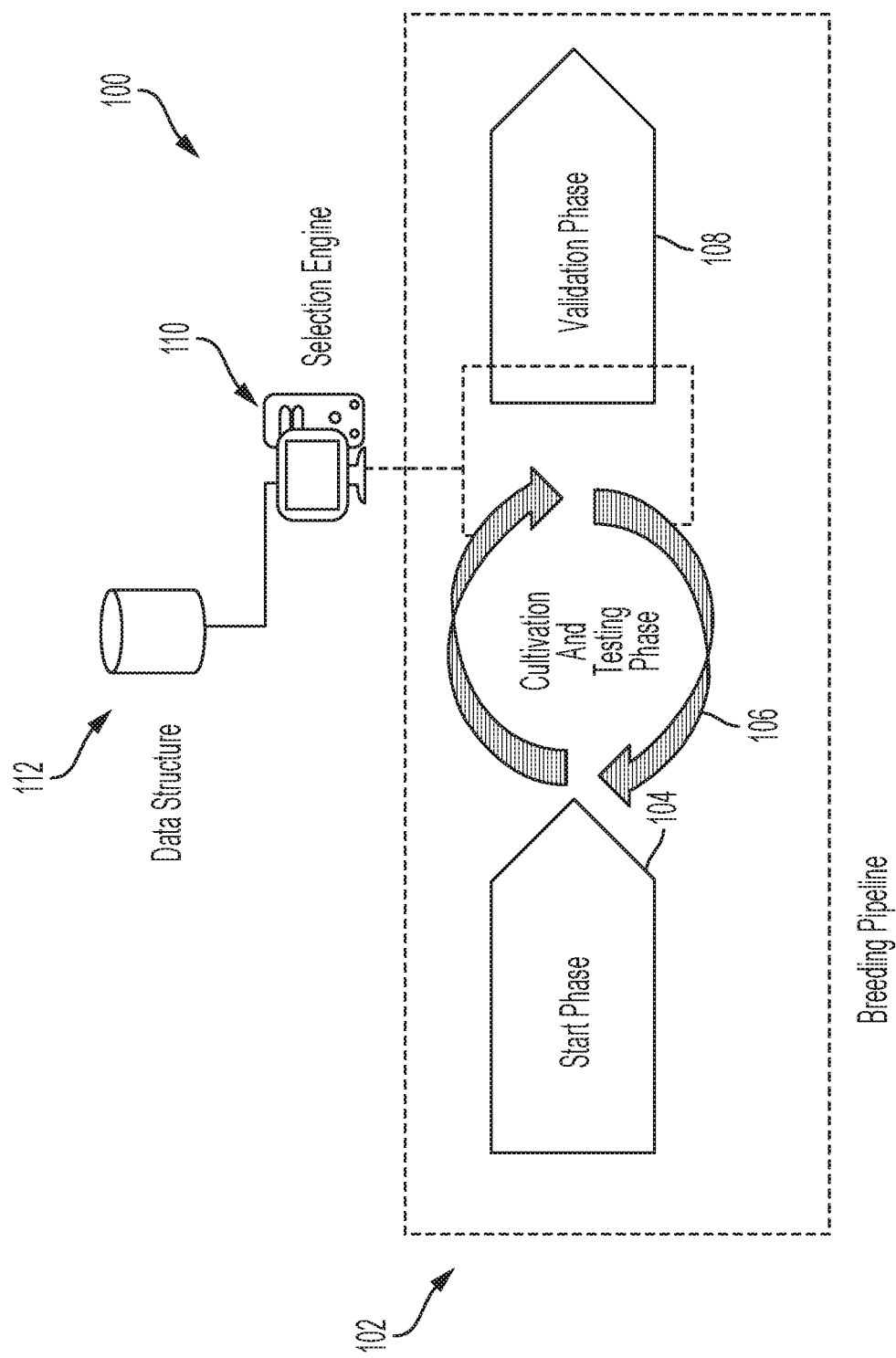
FIG. 1 illustrates an exemplary system of the present disclosure suitable for identifying a set of progenies from a pool of potential progenies for advancement in a breeding pipeline.

Exemplary embodiments will now be described more fully with reference to the accompanying drawings. The description and specific examples included herein are intended for purposes of illustration only and are not intended to limit the scope of the present disclosure.

Various breeding techniques are commonly employed in agricultural industries to produce desired progeny. Often, breeding programs implement such techniques to obtain progeny having desired characteristics or combinations of characteristics and/or traits (e.g., yield, stalk strength, disease resistance, etc.). However, it is difficult to accurately determine the best progeny when selecting a set of progenies from such programs, especially when a large number of options are available. For example, if a breeder is given N number of origins, and n number of progenies are created from each origin, the total number of progenies becomes N×n, where the goal may be to select r number of progenies for a breeding pipeline. As such, assuming and/or taking into account certain phenotypic data related to the progenies, such as, for example, yield, height, stability, or other data, (such as genetic data for example) related to other plants, each of the progenies might be evaluated whereby there could be as many as $$C_r^{nN} = \frac{nN!}{(nN-r)!r!}$$

distinct sets of progenies, which may be reduced to $$\sim \left(\frac{nN}{r}\right)^r.$$

In the case of a potential real world example, where N=100, n=10, and r=100, the complexity is quantified at $10^{100}$. As can be seen from this example, the selection of progenies accounts for substantial complexity, especially when it is required and/or desired to account for trait distribution and/or genetic diversity.

Uniquely, the methods and systems herein permit identification of a set of progenies, from a pool of progenies, to be included in a breeding pipeline. In particular, the pool of progenies is reduced, initially, for example, to a group of progenies based on a prediction score for each of the progenies, which is indicative of a success of the progeny based on past selections of progenies (e.g., based on phenotypic data, etc.) and/or available relevant data associated with the progenies. Then, for the group of progenies (as initially reduced), a selection algorithm is employed to identify the set of the progenies to be advanced in the breeding pipeline. As such, complexities associated with the identification of progenies to be advanced in the breeding pipeline are addressed in a manner that is more efficient and more comprehensive than that of conventionally known techniques. As such, an optimal set of progenies may be identified, whereby the final optimal set balances expected performance of the progenies and genetic diversity among the progenies.

Progeny are generally organisms which descend from one or more parent organisms of the same species. Progeny may refer to, for example, a universe of all possible progenies from a particular breeding program, a subset of all possible progenies, or offspring from a plant which exhibits one or more different phenotypes, etc. Progenies may further include all offspring from a line and/or a cross in a given generation, certain offspring from a cross, or individual plants, etc.

As used herein, the term "origin" refers to the parent(s) of progeny, and is therefore interpreted as either singular or plural, as applicable. The phenotypic data, trait distribution, ancestry, genetic sequence, commercial success, and additional information of the origin are generally known and may be stored in memory described herein. Hereditary genetics indicate the traits of the parent(s) to be passed to the progeny. And, mutations, genetic recombination, and/or directed genetic modification may alter the genotype and resulting phenotype of the progeny vis-à-vis the origin.

"Phenotypic data" as used herein includes, but is not limited to, information regarding the phenotype of a given progeny (e.g., a plant, etc.), or a population of progeny (e.g., a group of plants, etc.). Phenotypic data may include the size and/or heartiness of the progeny (e.g., plant height, stalk girth, stalk strength, etc.), yield, time to maturity, resistance to biotic stress (e.g., disease or pest resistance, etc.), resistance to abiotic stress (e.g., drought or salinity resistance, etc.), growing climate, or any additional phenotypes, and/or combinations thereof.

It should be appreciated that the methods and systems herein generally involve the phenotypic data associated with one or more progenies, crosses, lines, etc. That said, it should be appreciated that genotypic data may be used, in connection or in combination with the phenotypic data described herein (or otherwise) (e.g., to further supplement the phenotypic data and/or to further inform the models, algorithms, and/or predictions herein, etc.), in one or more exemplary implementations, to aid in the selection of groups of progenies and/or identification of sets of progenies consistent with the description herein.

FIG. 1 illustrates an exemplary system 100 for selecting progenies, in which one or more aspects of the present disclosure may be implemented. Although, in the described embodiment, parts of the system 100 are presented in one arrangement, other embodiments may include the same or different parts arranged otherwise depending, for example, on particular characteristics and/or traits of interest in the progenies, particular genetic diversity of the progenies, particular types of plants and/or progenies of interest, etc.

As shown in FIG. 1, the system 100 generally includes a breeding pipeline 102, which is provided to select a set of progenies from a pool of progenies to be advanced toward commercial product development. The breeding pipeline 102 generally defines a pyramidal progression, whereby it starts with a large number of potential progenies and successively narrows (e.g., reduces) the number of potential progenies to preferred and/or desired progenies. While the breeding pipeline 102 is configured to employ the selections provided herein, the breeding pipeline 102 may be configured to employ one or more other techniques which may include a wide range of methods known in the art, often depending on the particular plant and/or organism for which the breeding pipeline 102 is provided.

In certain breeding pipeline embodiments (e.g., large industrial breeding pipelines, etc.), testing, selections, and/or advancement may be directed to hundreds, thousands, or more origins, progenies, etc., in multiple phases and at several locations over several years to arrive at a reduced set of origins, progenies, etc., which are then selected for commercial product development. In short, the breeding pipeline 102 is configured, by the testing, selections, etc., included therein, to reduce a large number of origins, progenies, etc., down to a relatively small number of superior-performing commercial products.

In this exemplary embodiment, the breeding pipeline 102 is described with reference to, and is generally directed to, corn or maize and traits and/or characteristics thereof. However, it should be appreciated that the systems and methods disclosed herein are not limited to corn and may be employed in a plant breeding pipeline/program relating to other plants, for example, to improve any fruits, vegetables, grasses, trees, or ornamental crops, including, but not limited to, maize (*Zea mays*), soybean (*Glycine max*), cotton (*Gossypium hirsutum*), peanut (*Arachis hypogaea*), barley (*Hordeum vulgare*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g., species: *Agrostis stolonifera, Poa pratensis, Stenotaphrum secundatum*, etc.); wheat (*Triticum aestivum*), and alfalfa (*Medicago sativa*), members of the genus *Brassica*, including broccoli, cabbage, cauliflower, canola, and rapeseed, carrot, Chinese cabbage, cucumber, dry bean, eggplant, fennel, garden beans, gourd, leek, lettuce, melon, okra, onion, pea, pepper, pumpkin, radish, spinach, squash, sweet corn, tomato, watermelon, honeydew melon, cantaloupe and other melons, banana, castorbean, coconut, coffee, cucumber, Poplar, Southern pine, *Radiata* pine, Douglas Fir, *Eucalyptus*, apple and other tree species, orange, grapefruit, lemon, lime and other citrus, clover, linseed, olive, palm, *Capsicum, Piper*, and Pimenta peppers, sugarbeet, sunflower, sweetgum, tea, tobacco, and other fruit, vegetable, tuber, and root crops. The methods and systems herein may also be used in conjunction with non-crop species, especially those used as model methods and/or systems, such as *Arabidopsis*. What's more, the methods and systems disclosed herein may be employed beyond plants, for example, for use in animal breeding programs, or other non-plant and/or non-crop breeding programs.

As shown in FIG. 1, the breeding pipeline 102 includes a progeny start phase 104 and a cultivation and testing phase 106, which together identify and/or select one or multiple progenies for advancement to a validation phase 108. In the validation phase 108, then, the progenies are introduced into pre-commercial testing as progenies, lines, or as hybrids, for example, depending on the particular type of progenies, or other suitable processes (e.g., a characterization and/or commercial development phase, etc.) with an end goal and/or target to be planting and/or commercialization of the progenies. With that said, it should be appreciated that the breeding pipeline 102 may include a variety of conventional processes known to those skilled in the art in the three different phases 104, 106, and 108 illustrated in FIG. 1.

In the progeny start phase 104, a pool of potential progenies is provided from one or more sets of origins. The origins may be selected by a breeder, for example, or otherwise, depending on the particular type of plant, etc. The origins may also be selected, for example, based on origin selection systems and/or based (at least in part) on the methods and systems disclosed in U.S. patent application Ser. No. 15/618,023, titled "Methods for Identifying Crosses for use in Plant Breeding," the entire disclosure of which is incorporated herein by reference. Once the origins are selected, the pool of progenies is created from multiple crosses of the origins. The pool of progenies is then directed to the cultivation and testing phase 106, in which the progenies are planted or otherwise introduced into one or more growing spaces, such as, for example, greenhouses, shade houses, nurseries, breeding plots, fields (or test fields), etc. As needed, in some applications of the breeding pipeline 102, the pool of progenies may be combined with one or more tester plants, to yield a plant product suitable for introduction into the cultivation and testing phase 106.

Once the progenies are grown in the cultivation and testing phase 106, each is tested (again as part of the cultivation and testing phase 106 in this example) to derive and/or collect phenotypic data for the progeny, whereby the phenotypic data is stored in one or more data structures, as described below. In connection therewith, the testing may include, for example, any suitable techniques for determining phenotypic data. Such techniques may include any number of tests, trials, or analyses known to be useful for evaluating plant performance, including any phenotyping known in the art. In preparation for such testing, samples of embryo and/or endosperm material/tissue may be harvested/removed from the progenies in a way that does not kill or otherwise prevent the seeds or plants from surviving the ordeal. For example, seed chipping may be employed to obtain tissue samples from the progenies for use in determining desired phenotypic data. Any other methods of harvesting samples of tissue can also be used, as conducting assays directly on the tissue of the seeds that do not require samples of tissue to be removed. In certain embodiments, the embryo and/or endosperm remain connected to other tissue of the seeds. In certain other embodiments, the embryo and/or endosperm are separated from other tissue of the seeds (e.g., embryo rescue, embryo excision, etc.). Common examples of phenotypes that may be assessed through such testing include, without limitation, disease resistance, abiotic stress resistance, yield, seed and/or flower color, moisture, size, shape, surface area, volume, mass, and/or quantity of chemicals in at least one tissue of the seed, for example, anthocyanins, proteins, lipids, carbohydrates, etc., in the embryo, endosperm or other seed tissues. As an example, where a progeny (e.g., cultivated from a seed, etc.) has been selected or otherwise modified to produce a particular chemical (e.g., a pharmaceutical, a toxin, a fragrance, etc.), the progeny can be assayed to quantify the desired chemical.

With that said, it should be appreciated that the cultivation and testing phase 106 of the breeding pipeline 102 in the illustrated embodiment is not limited to certain or particular testing techniques, as any techniques suitable to aid in the determination of one or more characteristics and/or traits of the progeny at any stage of the life cycle may be used. In certain examples, it may be advantageous to use testing techniques which may be conducted without germinating a seed of the progeny or otherwise cultivating a plant sporophyte (e.g., via chipping of the seed as discussed above, etc.). It should further be appreciated that the cultivation and testing phase 106 may include multiple iterations, as indicated by the arrows in FIG. 1, in which crosses are grown and/or tested and selections are made, and whereby the pool of potential progenies is reduced. The testing performed within the cultivation and testing phase 106 may be adapted to include multiple iterations to provide the testing and/or data suitable to the progenies (e.g., particular types of progenies, etc.) and/or the techniques described herein.

With continued reference to FIG. 1, transition of a progeny from one cultivation and testing phase 106 to another, and/or to the validation phase 108, is controlled, in the system 100, by a selection engine 110. The selection engine 110 includes at least one computing device, which may be a standalone computing service, or may be a computing device integrated with one or more other computing devices. The selection engine 110 facilitates control in identifying progenies to transition within the cultivation and testing phase 106 from one iteration to another iteration (e.g., between a testing and cultivation cycle having one or multiple iterations, etc.) (as indicated by the circled arrows), and/or progenies to transition to the validation phase 108 (as indicated by the dotted indicator), and more generally progression from one phase to the next. The selection engine 110 is configured, by computer-executable instructions and/or one or more algorithms provided herein (or variants thereof or others), to perform the operations described herein.

In addition, the system 100 further includes a progeny data structure 112 coupled to the selection engine 110. In this exemplary embodiment, the progeny data structure 112 includes data related to the progeny, the underlying origins, and further ancestors and/or related origins, progenies, etc. The data may include any type of data for the progenies, origins, etc., related, for example, to the origin of the plant material, testing of the plant material, etc. The data structure 112 may include data consistent with a present growing/testing cycle and may include data related to prior growing/testing cycles. For example, that data structure 112 may include data indicative of various different characteristics and/or traits of the plants for the current and/or the last one, two, five, ten, fifteen, or more or less years of the plants through the cultivation and testing phase 106, or other growing spaces included in or outside the breeding pipeline 102, and also present data from the cultivation and testing phase 106. Table 1 illustrates exemplary historical phenotypic data from a series of maize plants (as may be included in the data structure 112), where a variable value is provided for yield of the plant, height of the plant, and standability of the plant (but where such variables could include additionally (or alternatively) include, for example, pods per plant, oil content and/or protein content for soy bean plants, etc.). It should be appreciated that other data, and specifically, phenotypic data, may be included in the data structure 112 for both maize plants and other types of plants, as contemplated herein.

TABLE 1

| Plant | Yield | Height | Stand | Historical |
|-------|-------|--------|-------|------------|
| $P_1$ | $Y_1$ | $H_1$  | $S_1$ | True       |
| $P_2$ | $Y_2$ | $H_2$  | $S_2$ | False      |
| $P_3$ | $Y_3$ | $H_3$  | $S_3$ | False      |
| $P_4$ | $Y_4$ | $H_4$  | $S_4$ | True       |
| $P_5$ | $Y_5$ | $H_5$  | $S_5$ | True       |
| ...   | ...   | ...    | ...   | ...        |

As mentioned above, the phenotypic data included in Table 1 is historical data (e.g., compiled through current and/or prior breeding cycles and/or experimentation in current and/or past years, cycles, etc.). As a result, in addition to the specific phenotypic data, Table 1 of the data structure 112 further includes an advancement decision for the plant associated with the data. As shown in Table 1, plants $P_1$, $P_4$, and $P_5$ were advanced (based on the True indication) in a breeding pipeline in a previous season, year, or other cycle, while plants $P_2$ and $P_3$ were not. In other words, the historical data in Table 1 also includes the historical selection of the progenies, where TRUE indicates the progeny was advanced in the breeding process and where FALSE indicates the progeny was not advanced in the breeding process.

In this exemplary embodiment, the selection engine 110 is configured to generate a prediction model, based on the historical data, in whole or in part, included in the data structure 112 and/or provided via one or more user inputs, decisions, and/or iterations, where the prediction model indicates a probability of an origin, progeny, etc., for example, being "advanced" (e.g., to the validation phase 108, etc.) as defined in the past based on a set of data, such as, for example, phenotypic data. The selection engine 110 may employ any suitable technique and/or algorithm to generate the prediction model (also referred to as a prediction algorithm). The techniques may include, without limitation, random forest, support vector machine, logistic regression, tree based algorithms, naïve Bayes, linear/logistic regression, deep learning, nearest neighbor methods, Gaussian process regression, and/or various forms of recommendation systems techniques, methods and/or algorithms (See "Machine learning: a probabilistic perspective" by Kevin P. Murphy (MIT press, 2012), which is incorporated herein by reference in its entirety, to provide a manner of determining a probability of advance for a given set of data (e.g., yield, height, and standability for maize, etc.)).

As an example, and as described in more detail below, the prediction model herein may be consistent with the random forest technique. The random forest technique is an ensemble of multiple decision tree classifiers. Each of the decision trees are trained on randomly sampled data from a training data set (e.g., such as included in Table 1, etc.). Further, a random subset of features (e.g., as indicated by the phenotypic data, etc.) may then be selected to generate the individual trees. The final prediction model, generated by the random forest, is computed, by the selection engine 110, as an aggregation of the individual trees. It should be appreciated that the selection engine 110 is configured to generate the model (and different iterations of the model) based on further user inputs (e.g., related to the trees, parameters, etc.), etc., until a satisfactory prediction model is generated/achieved. In another example, the prediction model herein may include or utilize the support vector machine (SVM) technique, which is provided to classify the lines into positive and negative classes based on the phenotypes. Here, the prediction model (or SVM model) training involves solving a convex optimization problem, which finds the optimal hyperplane (linear or nonlinear), which would be able to separate the positive and negative samples, based on the phenotypic data, which may then be selected from the model, as described below.

In any case, once the prediction model is generated, the selection engine 110 further is configured to determine a prediction score, based on the prediction model, for each of the progenies in the pool of progenies introduced in the progeny start phase 104 and included in the cultivation and testing phase 106. Specifically, when the pool of progenies is tested, in the cultivation and testing phase 106, phenotypic data (e.g., yield, height, standability, etc.), or generally, data related to the progenies, is gathered and stored in the data structure 112. In determining a prediction score, the selection engine 110 is configured to access the data structure 112 and to retrieve data related to the progenies included in the pool. From that data and from application of the prediction model thereto, the selection engine 110 is configured to determine a prediction score. Table 2 illustrates the exemplary progenies that may be included in the pool in this example, which are designated $A_1/A_2$@0001, $A_1/A_2$@0002 through $A_1/A_2$@000n, and $A_3/A_4$@0001 through $A_3/A_4$@000n, etc. The origins of the progenies and certain phenotypic data for each of the progenies is also included.

TABLE 2

| Progeny | Origin | Yield | Height | Stand | Selection |
|---------|--------|-------|--------|-------|-----------|
| $A_1/A_2$@0001 | $A_1/A_2$ | $Y_1$ | $H_1$ | $S_1$ | True |
| $A_1/A_2$@0002 | $A_1/A_2$ | $Y_2$ | $H_2$ | $S_2$ | False |
| ... | ... | ... | ... | ... | ... |
| $A_1/A_2$@000n | $A_1/A_2$ | $Y_n$ | $H_n$ | $S_n$ | False |
| $A_3/A_4$@0001 | $A_3/A_4$ | $Y_{n+1}$ | $H_{n+1}$ | $S_{n+1}$ | True |
| ... | ... | ... | ... | ... | ... |
| $A_3/A_4$@000n | $A_3/A_4$ | $Y_{2n}$ | $H_{2n}$ | $S_{2n}$ | False |
| ... | ... | ... | ... | ... | ... |

That said, it should be appreciated that the selection engine 110 may be configured to determine the prediction score based on ranking phenotypic data and/or on derived phenotypic data (e.g., best linear unbiased prediction (BLUP), etc.) associated with the progenies included in the data structure 112. In such embodiments, the data is ranked with a top X number of progenies selected for advancement herein, whereby the rank is employed as a prediction score (e.g., TRUE/FALSE, etc.) for each progeny above a threshold (as compared to any modeling of the data included in the data structure 112).

Then in the operation of the breeding pipeline 102 (in accordance with the present disclosure), based on the determined prediction scores, the selection engine 110 is configured to select ones of the progenies (from the pool) to be included in a group of progenies. The selection may be based on the prediction scores relative to one or more thresholds, or it may be based on the prediction scores relative to one another, or otherwise. In Table 2, the progenies selected to the group of progenies, by the selection engine 110 (based on the determined prediction scores), are designated TRUE, while the progenies not selected to the group of progenies, by the selection engine 110, are designated FALSE.

The selection engine 110 is further configured to identify a set of progenies, from the group of progenies, to advance to a next iteration of the cultivation and testing phase 106 and/or to advance to the validation phase 108. To do so, the selection engine 110 is configured to employ one or more additional algorithms, as described herein or otherwise, for example, to account for a predicted performance of the particular progeny (e.g., based on the prediction score, etc.), and further based on, optionally, for example, a risk associated with the progeny, and/or a deviation of the identified progeny from a desired and/or preferred profile of performance (e.g., related to origins, pedigree, family, etc.), or other factors indicative of a desired progeny for such selection (e.g., individual traits, multiple traits, product cost (e.g., cost of goods, etc.), market segmentation needs/desires, commercial breeding decisions, trait available and/or readiness, etc.), etc. When suitable, the selection engine 110 may be configured to perform further iterations of the cultivation and testing phase 106, as needed, to identify the set of progenies such that a desired number of progenies is included therein.

Finally, in the breeding pipeline 102, the identified progenies from the selection engine 110 (in the set of progenies) are advanced to the validation phase 108, in which the progenies are exposed to pre-commercial testing or other suitable processes (e.g., a characterization and/or commercial development phase, etc.) with a goal and/or target to be planting and/or commercialization of the progenies. That is, the set of progenies may then be subjected to one or more additional/further tests and/or selection methods, trait integration operations, and/or bulking techniques to prepare the progenies, or plant material based thereon, for further testing and/or commercial activities. In one specific embodiment, one or more plants, derived from the identified progenies, are included in at least one growing space of the breeding pipeline 102, whereby the one or more plants are grown and subject to further testing and/or commercial activities.

What's more, it should be appreciated that the selection engine 110 may be configured to provide (e.g., generate and cause to be displayed at a computing device of a breeder, etc.) and/or respond to a user interface, through which a breeder (broadly, a user) is able to make selections and provide inputs regarding progenies or desired traits for progenies for use herein. The user interface may be provided directly at a computing device (e.g., computing device 200 as described below, etc.) associated with the breeder, in which the selection engine 110 is employed, or via one or more network-based applications through which a remote user (again, potentially a breeder) may be able to interact with the selection engine 110 as described herein.

Figure 2:
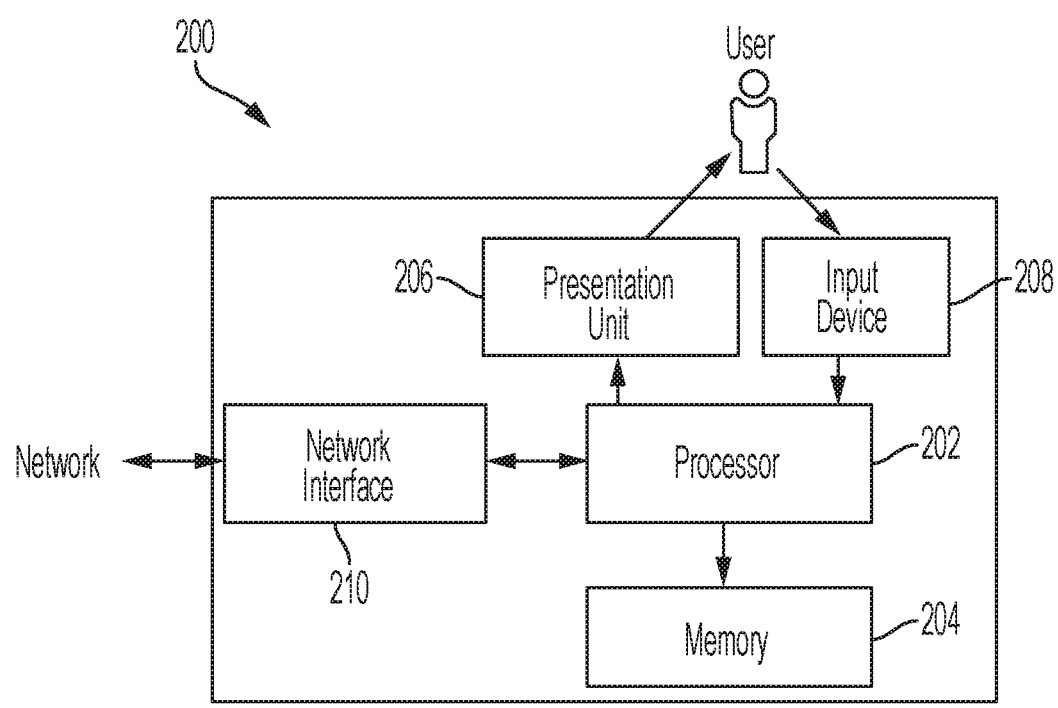
FIG. 2 is a block diagram of a computing device that may be used in the exemplary system of FIG. 1.

FIG. 2 illustrates an exemplary computing device 200 that may be used in the system 100, for example, in connection with various phases of the breeding pipeline 102, in connection with the selection engine 110, the progeny data structure 112, etc. For example, at different parts of the breeding pipeline 102, breeders or other users interacting with computing devices, consistent with computing device 200, enter data and/or access data in the progeny data structure 112 to support breeding decisions and/or testing completed/accomplished by such breeders or other users. In connection therewith, the selection engine 110 of the system 100 includes at least one computing device consistent with computing device 200. The computing device 200 may be configured, by executable instructions, to implement the various algorithms and other operations described herein with regard to the selection engine 110. It should be appreciated that the system 100, as described herein, may include a variety of different computing devices, either consistent with computing device 200 or different from computing device 200.

The exemplary computing device 200 may include, for example, one or more servers, workstations, personal computers, laptops, tablets, smartphones, other suitable computing devices, combinations thereof, etc. In addition, the computing device 200 may include a single computing device, or it may include multiple computing devices located in close proximity or distributed over a geographic region, and coupled to one another via one or more networks. Such networks may include, without limitations, the Internet, an intranet, a private or public local area network (LAN), wide area network (WAN), mobile network, telecommunication networks, combinations thereof, or other suitable network(s), etc. In one example, the progeny data structure 112 of the system 100 includes at least one server computing device, while the selection engine 110 includes at least one separate computing device, which is coupled to the progeny data structure 112, directly and/or by one or more LANs, etc.

With that said, the illustrated computing device 200 includes a processor 202 and a memory 204 that is coupled to (and in communication with) the processor 202. The processor 202 may include, without limitation, one or more processing units (e.g., in a multi-core configuration, etc.), including a central processing unit (CPU), a microcontroller, a reduced instruction set computer (RISC) processor, an application specific integrated circuit (ASIC), a programmable logic device (PLD), a gate array, and/or any other circuit or processor capable of the functions described herein. The above listing is exemplary only, and thus is not intended to limit in any way the definition and/or meaning of processor.

The memory 204, as described herein, is one or more devices that enable information, such as executable instructions and/or other data, to be stored and retrieved. The memory 204 may include one or more computer-readable storage media, such as, without limitation, dynamic random access memory (DRAM), static random access memory (SRAM), read only memory (ROM), erasable programmable read only memory (EPROM), solid state devices, flash drives, CD-ROMs, thumb drives, tapes, hard disks, and/or any other type of volatile or nonvolatile physical or tangible computer-readable media. The memory 204 may be configured to store, without limitation, the progeny data structure 112, phenotypic data, testing data, set identification algorithms, origins, various threshold, prediction models, and/or other types of data (and/or data structures) suitable for use as described herein, etc. In various embodiments, computer-executable instructions may be stored in the memory 204 for execution by the processor 202 to cause the processor 202 to perform one or more of the functions described herein, such that the memory 204 is a physical, tangible, and non-transitory computer-readable storage media. It should be appreciated that the memory 204 may include a variety of different memories, each implemented in one or more of the functions or processes described herein.

In the exemplary embodiment, the computing device 200 also includes a presentation unit 206 that is coupled to (and is in communication with) the processor 202. The presentation unit 206 outputs, or presents, to a user of the computing device 200 (e.g., a breeder, etc.) by, for example, displaying and/or otherwise outputting information such as, but not limited to, selected progeny, progeny as commercial products, and/or any other types of data as desired. It should be further appreciated that, in some embodiments, the presentation unit 206 may comprise a display device such that various interfaces (e.g., applications (network-based or otherwise), etc.) may be displayed at computing device 200, and in particular at the display device, to display such information and data, etc. And in some examples, the computing device 200 may cause the interfaces to be displayed at a display device of another computing device, including, for example, a server hosting a website having multiple webpages, or interacting with a web application employed at the other computing device, etc. Presentation unit 206 may include, without limitation, a liquid crystal display (LCD), a light-emitting diode (LED) display, an organic LED (OLED) display, an "electronic ink" display, combinations thereof, etc. In some embodiments, presentation unit 206 may include multiple units.

The computing device 200 further includes an input device 208 that receives input from the user. The input device 208 is coupled to (and is in communication with) the processor 202 and may include, for example, a keyboard, a pointing device, a mouse, a stylus, a touch sensitive panel (e.g., a touch pad or a touch screen, etc.), another computing device, and/or an audio input device. Further, in some exemplary embodiments, a touch screen, such as that included in a tablet or similar device, may perform as both presentation unit 206 and input device 208. In at least one exemplary embodiment, the presentation unit and input device may be omitted.

In addition, the illustrated computing device 200 includes a network interface 210 coupled to (and in communication with) the processor 202 (and, in some embodiments, to the memory 204 as well). The network interface 210 may include, without limitation, a wired network adapter, a wireless network adapter, a telecommunications adapter, or other device capable of communicating to one or more different networks. In at least one embodiment, the network interface 210 is employed to receive inputs to the computing device 200. For example, the network interface 210 may be coupled to (and in communication with) in-field data collection devices, in order to collect data for use as described herein. In some exemplary embodiments, the computing device 200 may include the processor 202 and one or more network interfaces incorporated into or with the processor 202.

Figure 3:
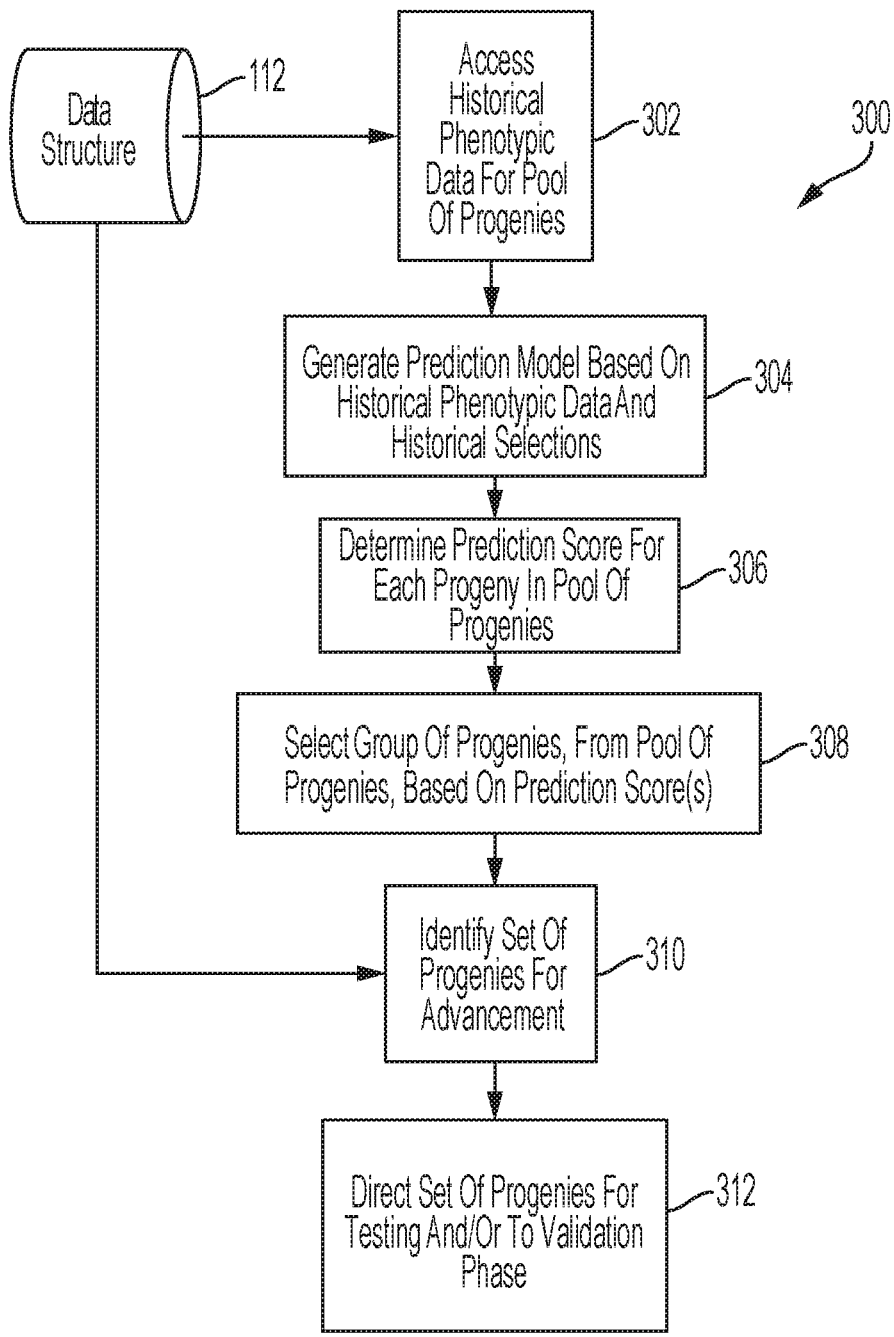
FIG. 3 is an exemplary method, suitable for use with the system of FIG. 1, for identifying a set of progenies from a pool of potential progenies.

FIG. 3 illustrates an exemplary method 300 of selecting progenies in a progeny identification process. The exemplary method 300 is described herein in connection with the system 100, and may be implemented, in whole or in part, in the selection engine 110 of the system 100. Further, for purposes of illustration, the exemplary method 300 is also described with reference to the computing device 200 of FIG. 2. However, it should be appreciated that the method 300, or other methods described herein, are not limited to the system 100 or the computing device 200. And, conversely, the systems, data structures, and the computing devices described herein are not limited to the exemplary method 300.

To begin, a breeder (or other user) initially identifies a plant type (e.g., maize, soybeans, etc.) and one or more desired phenotypes, potentially consistent with one or more desired characteristics and/or traits to be advanced in the identified plant, or a desired performance in a commercial plant product. In turn, based on the above and/or one or more other criteria, the breeder or user, alone or through various processes, selects a set of origins to be a starting point for the selection of progenies (based on the initial identification). Then, for a given population of origins, a number of crosses are identified from which a group of progenies is provided as input to the exemplary method 300.

Figure 4:
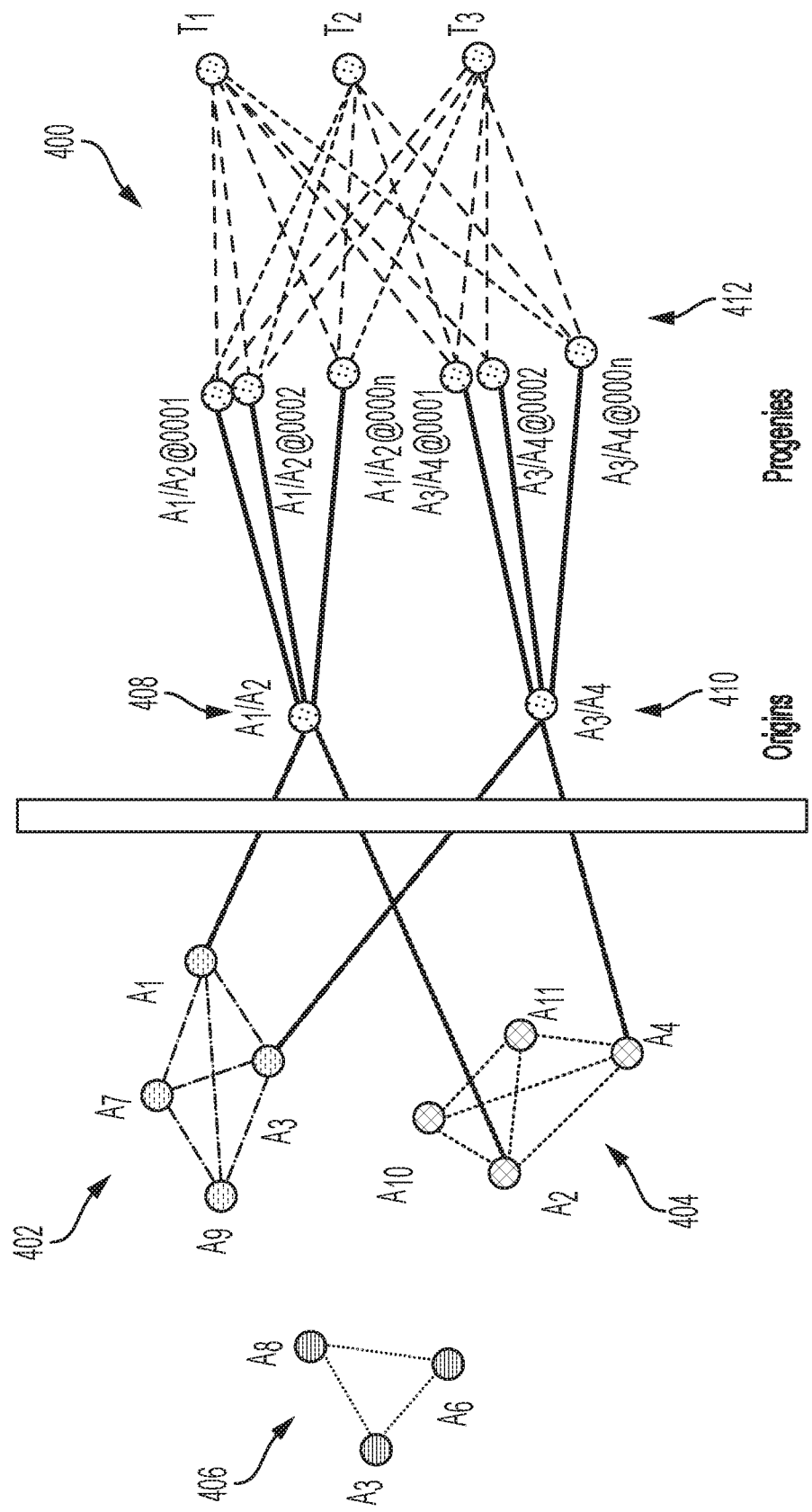
FIG. 4 is a graphical representation of an exemplary set of origins being combined to provide a series of progenies, from which certain of the progenies may be selected through the method of FIG. 3.

As an example of such identification (for input into the method 300), FIG. 4 illustrates lines $A_1$ through $A_{11}$ arranged into different clusters, where the clusters (in this example) are indicative of genetic relatedness. Here, certain crosses/origins $A_1/A_2$ and $A_3/A_4$, for example, may be identified for advancement via the method 300. Specifically, the lines are selected from different genetic relatedness clusters 402, 404, 406 to promote genetic diversity, or based on commercial success, or based on other characteristics and/or traits, etc. And, the crosses/origins 408, 410 provide multiple progenies 412, which are designated $A_1/A_2$@0001, $A_1/A_2$@0002 through $A_1/A_2$@000n, and $A_3/A_4$@0001, $A_3/A_4$@0002 through $A_3/A_4$@000n, etc. Each of the progenies from the crosses is distinct, but related.

In this example, each of the progenies 412 is included in a hybrid (e.g., a maize hybrid, etc.), whereby each of the progenies is combined with a tester for purposes of testing. Specifically, as shown, the testers $T_1$, $T_2$, and $T_3$ are employed, as known origins/plants, for use in creating a plant product for planting. It should be appreciated that for certain progenies (e.g., soybeans, etc.), testers may be omitted. Regardless of whether testers are used, or not, the progenies are planted in a field, laboratory, or other growing space, and grown. As the plant products from the progenies are grown, certain phenotypic data for the progenies are measured, gathered and/or obtained through testing, and then stored in the data structure 112, directly or via the selection engine 110.

With this input, the selection engine 110 then employs the method 300 to ultimately identify a set of the progenies (e.g., 100 progenies, etc.) for advancement in the breeding pipeline 102, for example. Further, as a basis for illustrating the method 300, one hundred origins may be selected for use, with ten progenies from each combination of the origins, with an aim to select one hundred progenies to advance. This example gives rise to $10^{100}$ different potential sets of identified progenies.

As shown in FIG. 3, at 302 in the method 300, the selection engine 110 initially accesses historical data for a pool of progenies within the data structure 112 (e.g., historical data for a pool of available progeny for the breeding pipeline 102 consistent with the breeder's desires, etc.). This may include both historical data and present data. For example, the accessed data may include the historical data for the exemplary progenies of Table 1, which are consistent with the progenies illustrated in FIG. 4 or distinct therefrom, and which was compiled through current and/or prior breeding cycles and/or experimentation in current and/or past years, cycles, etc. Once accessed, the selection engine 110 generates, at 304, a prediction model based on the accessed historical phenotypic data (broadly, input data) and the corresponding historical selections of the progenies (broadly, response variable(s)), which, in use, then provides a prediction score for a given progeny that the progeny would have been selected for advancement for given phenotypic data. The model (or prediction algorithm) may be generated, by the selection engine 110, through one or more different supervised, unsupervised, or semi-supervised algorithms/models such as, but not limited to, random forests, support vector machines, logistic regressions, neural networks, tree based algorithms, naïve Bayes, linear/logistic regressions, deep learning, nearest neighbor methods, Gaussian process regressions, and/or various forms of recommendation system algorithms (which are incorporated herein by reference in their entirety), with each of such algorithms generally suited to classify and/or cluster data upon which the algorithm operates.

In particular, for example, the prediction scoring model may be generated to provide a likelihood that a given progeny will advance to a next and/or through a specific phase of the breeding pipeline 102. In connection therewith, a user begins with the accessed data set of relevant progenies from the historical data. This data set would need to include phenotypic data (and, potentially, genotypic data) for the progenies (again, input data). The input data would form the features on which the model is trained and on which the model will rely to make predictions for future progenies. The data set also includes a response variable, which indicates whether or not each progeny advanced from one particular phase and/or stage within the breeding pipeline 102 (or other similar breeding pipeline) (e.g., whether it advanced from the validation phase 108, whether it advanced from a commercial product, etc.). The advancement phase may be selected, by the user, to be indicative of a particular aim of implementation of the method 300. If multiple phases and/or stages exist, it should be appreciated that a composite response variable may be employed, whereby advancement into each phase/stage makes up a portion of the final response value included for each of the progenies in the data set.

It should be appreciated that the particular phenotypic data included in the data set may vary depending on the particular progenies included, the degree of correlation between phenotypic data and advancement, importance of the phenotypic data, etc.

Once this data set is provided with the input data and response variable, the user segregates the data set, either randomly or along a logical delineation (e.g., year, month, etc.), into a training set, a validation set, and a testing set. The data set may be segregated, for example, into a set ratio of 70:20:10, respectively (or otherwise). With these three distinct data sets, the modeling is initiated for the training set of data by the selection of an algorithm, as listed above. If, for example, a random forest is selected as a potential algorithm for creating this prediction score, the user, in general, selects a well-supported coding package that implements random forests in a suitable coding language, such as R or python. Once the package and the language have been selected, for example scikit-learn in python, the user commences the process of building the code framework to specify, build, train, validate, and test the model.

When the framework is built, it is connected to the training data set, the validation set, and the testing set, in their appropriate locations. Thereafter, the algorithm hyperparameters, which are the parameters that define the structure of the algorithm itself, are tuned. Some random-forest-specific examples of these hyperparameters include tree size, number of trees, and number of features to consider at each split, but the specific nature of the hyperparameters will vary from algorithm to algorithm (and/or based on user inputs, phenotypes, etc.). To begin the tuning process, the model is trained using an initial set of hyperparameters—which can be chosen based on past experience, an educated guess, at random, or by other suitable manner, etc. During the training process, the algorithm will attempt to minimize the error between the classifications it is making and the true response values included in the data set. Once this process is complete, the error rate reported from the training process is validated through evaluation of the error rate of the trained model on the separate validation data set. Close agreement of the error rates between the training and validation results can indicate the successful training of a generalized model, while strong divergence between the two (e.g., where the validation error rates are much higher than the training error rates) can indicate that the model may have been overfit to the training data. In order to address any overfitting or just to explore whether other hyperparameters may provide lower error rates, the user may repeat the training and validation process using different sets of hyperparameters while tracking of how the error rates associate with the different hyperparameters. Often, the user, as will be appreciated by those skilled in the art, is looking for the set of hyperparameters that enhance model performance (and limit error rates, as an example) without exhibiting signs of overfitting (e.g., strong divergence between performance on the training and validation sets might indicate overfitting). In order to further increase confidence in the generalizability of the resulting model, the user may repeat the above process for any of a number of different subsets of training and validation data sets (cross-validation).

Once a model is generated through the training, validation and/or cross-validation as described above (i.e., based on the training and validation data sets), the model is further evaluated on the test data set to determine an expected performance of the model on data that is, at that time, new, unseen data to the model. It should be appreciated that, in various embodiments, the test set is not used in the cross-validation or tuning process in order to provide and/or to ensure, as much as practical, that the test data has not been seen by the model previously (i.e., not generated based on the test data), that the evaluation of the model's performance on new data is reasonable, and that the model is efficient in predicting advancement of the progenies.

Next, as part of the method 300 or prior, if the performance of the model meets or exceeds expectations as defined, for example, by the user, a business need, etc., the model may then be employed to determine the prediction score, as provided below. Conversely, if the model does not perform as well as expected or if there exists a reasonable expectation that another algorithm may yield a model that has better or more efficient performance, the data scientist may instead decide to construct a prediction model with one or more different algorithms (e.g., a neural network, etc.) (as part of step 304) and then compare the final performance of the different models to determine which, if any, should be used in the remaining steps of method 300.

That said, it should be appreciated that the segregating of the data, hyperparameter tuning, and/or iterative modeling through different model types, may be done manually by the user or they may be done through one or more automated processes.

With continued reference to FIG. 3, then, the selection engine 110 access the data structure 112 again (or as part of step 302) to retrieve at least phenotypic data for the progenies, and then determines, at 306, a prediction score for each of the identified progenies (e.g., for the progenies designated $A_1/A_2$@0001, $A_1/A_2$@0002 through $A_1/A_2$@000n, $A_3/A_4$@0001, and $A_3/A_4$@0002 through $A_3/A_4$@000n in FIG. 4 and identified in Table 2, etc.), based on the model and the present phenotypic data gathered (e.g., from the data structure 112 or otherwise, etc.) and/or compiled from testing of the progenies in the growing space. The selection engine 110 then selects, at 308, a group of progenies from the pool of potential progenies, based on the prediction scores. In this exemplary embodiment, the progenies are indexed by the prediction scores in descending order, and the highest scored 10,000 progenies, for example, may be advanced to the filtered group. In other examples, the selection engine 110 may apply a threshold to the prediction scores to retain progenies with prediction scores that satisfy the threshold (e.g., are greater than the threshold, etc.), while discarding progenies with prediction scores that fail to satisfy the threshold.

With reference again to FIG. 4, the group of progenies 412 included therein is also indicated in Table 2 by TRUE and FALSE designations, where the TRUE progenies are included in the filtered group (at 308 in the method 300). As such, for example, progenies $A_1/A_2$@0001 and $A_3/A_4$@0001 are advanced into the filtered group (i.e., are designated as TRUE), while progenies $A_1/A_2$@0002, $A_1/A_2$@000n, and $A_3/A_4$@000n are not (i.e., are designated as FALSE).

In this exemplary embodiment, the selection engine 110, through the prediction score (and potentially one or more pre-prediction filters and/or restrictions, etc.), selects, generally, 100,000 or less progenies, 50,000 or less progenies, 20,000 or less progenies, 10,000 or less progenies, or 5,000 or less progenies, etc. for inclusion in the group of progenies, at 308. In one example, the pool of progenies includes approximately 10,000 progenies, from which about 6,000 or less are selected into a group of progenies, at 308. It should be appreciated that the number of progenies included in the group of progenies, as selected by the selection engine 110, may vary depending on, for example, the number of progenies in the pool, the type of progenies/plants, computation resources, etc., and may be different than any of the sizes provided above.

Next in the method 300, the selection engine 110 identifies, at 310, a set of progenies (from the filtered group of progeny), based on one or more selection algorithms. In this exemplary embodiment, the selection engine 110 employs A selection algorithm (Equation 1), where the total number of progenies includes N×n, and the set of progenies identified includes r progenies, and where $x_1$ is "1" if the first progeny is selected to the set, and "0" if the first progeny is not selected to the set:

$$X \in \{0,1\}^{nN} \tag{1}$$

In connection therewith, the selection engine 110 employs the following exemplary set identification algorithm (Equation 2) to identify the progenies to be included in the set of progenies. It should be appreciated that other set identification algorithms may be employed in other embodiments. Specifically, for example, as shown below, the set identification algorithm, at Equation 2, includes, initially, a term to account for the probability prediction scores of the progenies to be included in the set of progenies (i.e., the probability of success). In addition, the set identification algorithm includes further constraint terms which, in general, alter the set of progenies based on other factors of interest such as, for example, risk, genetic diversity (e.g., line distribution, etc.), trait(s) (e.g., presence, performance, etc.) (e.g., disease resistance, yield, etc.), probability of success of the base origins, probability of success of the base pedigrees, probability of success of the heterotic groups, trait profiles, market segmentation, product cost (e.g., cost of goods (COGS), etc.), trait integration, or other factors associated with the progenies, etc., in general through cost functions reduction to the term associated with the probability prediction score for the set of progenies (or by strict constraints (i.e., must be satisfied) included in a set identification algorithm, similar to Equation 2). Other set identification algorithms may include one or more of the factors above. In the example Equation 2, the set identification algorithm includes a term for risk.

$$x_{opt} = \underset{x \in \{0,1\}^{nN}}{\operatorname{argmax}} \left( \lambda_p \sum_{i=1}^{nN} x_i p_i - \lambda_r \sum_{i=1}^{nN} x_i r_i - \lambda_{d_1} 1^T \theta - \lambda_{d_2} 1^T \varphi - \lambda_{d_3} 1^T \gamma \right) \tag{2}$$

The term $\lambda_p \sum_{i=1}^{nN} x_i p_i$ of the set identification algorithm (Equation 2) accounts for the performance of the progenies, the term $\lambda_r \sum_{i=1}^{nN} x_i r_i$ accounts for risk, and the terms $\Delta_{d_1} 1^T \theta$, $\lambda_{d_2} 1^T \varphi$, and $\lambda_{d_3} 1^T \gamma$ account for deviations from one or more performance profiles. In addition, the term $p_i$ is indicative of a probability of success, and is generated by the prediction algorithm for progeny (or prediction model), as generated at 304. The $p_i$, and $r_i$ terms are associated with the performance and risk scores for individual progeny lines. The cost of each facilitates the selection of lines in the form of the decision variables $x_i$ such that the overall performance of the set of progenies is improved, desired, and/or maximized while risk is limited, reduced, or minimized (as compared to other sets of progenies). Without the last three terms in the cost, the cost would be maximized if the high performing and low risk lines are selected. However, in such circumstances, one or many diversity factors (at origin, base pedigree, or heterotic group levels) would be jeopardized. In addition, in order to maintain the diversity, and trait portfolios, the auxiliary variables θ, φ, and γ are introduced. These variables/factors act as penalty factors to the overall cost when the selections tend to fail to provide for diversities. The term $p_i$ is computed as a combination of the prediction score (determined at 306) and one or more phenotype traits. In this example, mutual information of the traits with respect to the historical decisions for advancement, or not, are used as weights. The weights are determined, for example, through mutual information between the historical decisions relating to selection (e.g., the TRUE/FALSE determinations in Table 1 above, etc.). And, one or more traits is used as the relative weight for a particular trait. Then, entropy is used as a measure of uncertainty in the probability distribution, where entropy for a variable x is defined by the following Equation 3:

$$H(x) = -\int p(x) \log p(x) dx \tag{3}$$

The mutual information of the two random variables x and y (e.g., the prediction score and the presence of a trait, etc.) is then defined through the following Equations 4 and 5:

$$I(X;Y) := =H(X) - H(X|Y) \tag{4}$$

$$= \int \int p(x, y) \log \frac{p(x, y)}{p(x)p(y)} dx d \tag{5}$$

Figure 5:
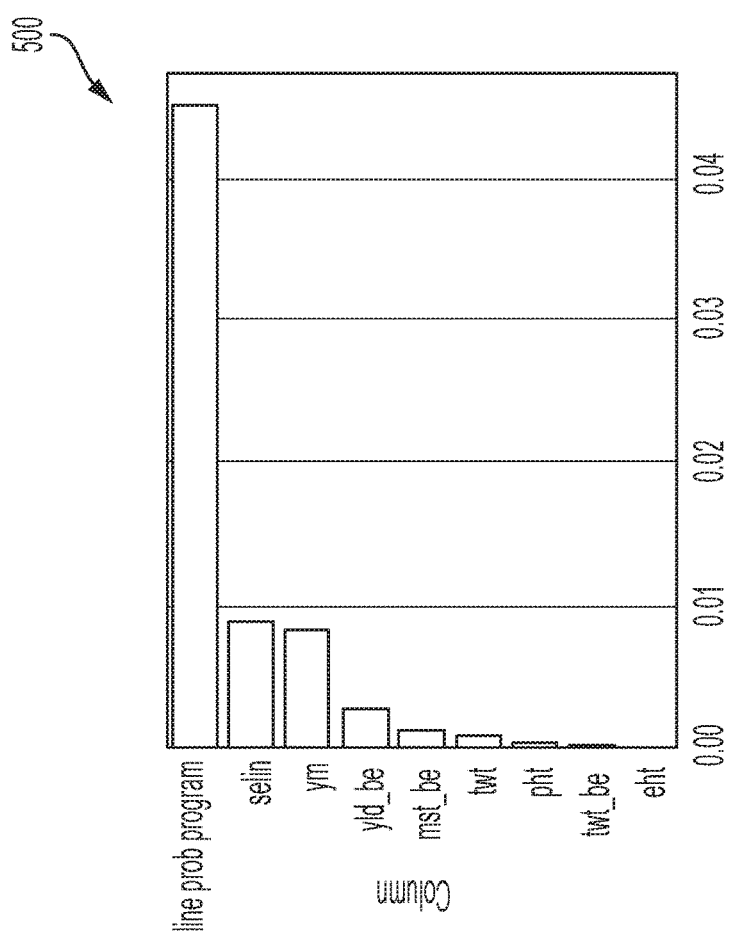
FIG. 5 is a graphical representation of mutual information between a prediction score, phenotypic traits, and a historical decision to advance a plant product to further breeding.

In this manner, the knowledge of the prediction score and/or the trait may reduce the uncertainly of one or more other variables (e.g., relevant to the probability of success of the progeny, etc.). For example, when the mutual information between the phenotypic traits, like yield, selection index, and the prediction score in one part and the historical decisions on the other part is determined, weights for the computation of the performance $p_i$ may be determined. In connection therewith, FIG. 5 illustrates mutual information of various traits of a progeny. As can be seen, the prediction score associated therewith shares maximum mutual information with the related historical decision for the progeny. Stated another way, the prediction score is able to be used to identify a potentially successful line to the maximal extent. Apart from the prediction score, selin and yield moisture ratio (ym) (and the other traits) have appreciable and/or predictive mutual information. These additional traits may thus be used to provide the performance score, for example, through weighting, as provided in the algorithm above. The mutual information is used in this exemplary embodiment because it provides suitable generalization and/or extends to discrete variables (e.g., a historical decision to advance, etc.) having nonlinear relationships with the prediction score and/or the trait(s). That said, other correlation techniques may be used in other method embodiments.

The term $p_i$ in the above equation (Equation 2) (as indicative of probability of success) then reflects a linear combination of dominant traits, where the weights, as shown in FIG. 4, for example, are defined by mutual information. In this manner, a more discrete manner of evaluating performance is provided for the group of progeny, as compared to the broader pool of progenies described above.

Figure 6:
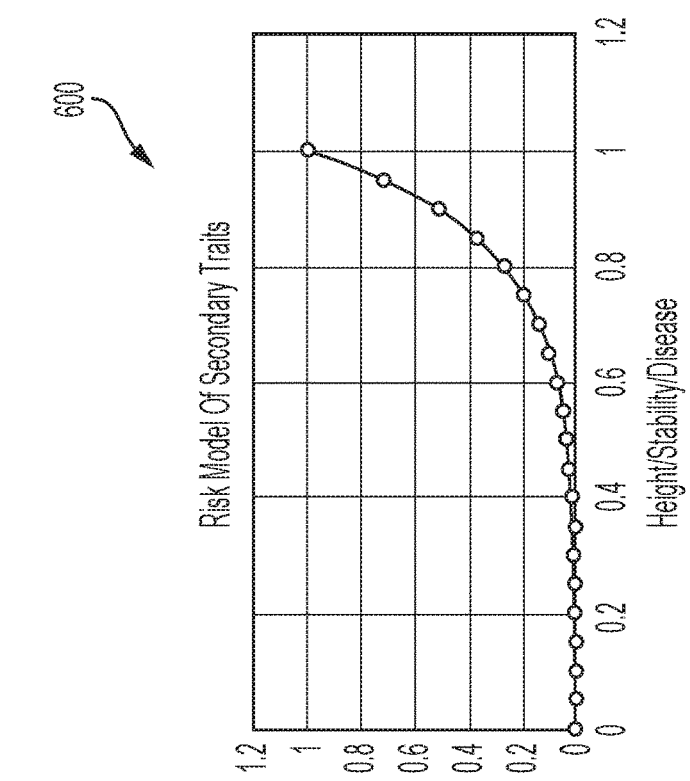
FIG. 6 illustrates an exemplary risk curve associated with multiple traits of hybrids included in the group of hybrids indicated or identified, for example, in connection with the method of FIG. 3.

The term $r_i$ in the above equation (Equation 2) is indicative of a risk of failure of progeny (e.g., is a risk vector, etc.). The risk is determined, by the selection engine 110, as an exponential function of the standability/height/disease traits (and/or the same of different suitable traits for maize or other plant types, etc.). Each is a negative trait and, generally, based on the method 300, the final set of progenies will include smaller values for these specific traits. The risk vector is normalized to ensure the values fall between 0 and 1 (e.g., with 0 being the least risky and 1 being the most risky, etc.). The risk is generally a probability of the failure despite apparently having high performance scores. FIG. 6, for example, illustrates a graph 600 indicating how the risk value of the progenies increases with increase in disease of certain traits (including standability traits, etc.). As shown, the growth is generally modeled as an exponential function.

Various additional equations (including Equations 13-15 below) may be used in connection with determining different terms of the set identification algorithm (Equation 2) above. In connection therewith (i.e., in connection with Equations 13-15 below), the term $o_i$ is indicative of a probability of success of a base origin. This term, in this exemplary embodiment, includes an average value of $p_j$ for all the progenies, which are coming from the i-th origin. This term can be computed, for example, through the following Equation 6:

$$o_i = \Sigma_j M_l(i,j) p_j \quad (6)$$

The term $b_i$ (and, consistent therewith, $b_k$ in Equation 14) is a probability of success of base pedigrees. This term, in this exemplary embodiment, includes an average value of $p_j$ for all the progenies, which are coming from an origin and which contain the i-th pedigree. This term can be computed, for example, through the following Equation 7:

$$b_i = \Sigma_j M_o(i,j) p_j \quad (7)$$

And, the term $h_i$ (and, consistent therewith, $h_j$ in Equation 15) is a probability of success of heterotic groups. This term, in this exemplary embodiment, includes an average value of $p_j$ for all the progenies, which are coming from the i-th heterotic group. This term can be computed, for example, through the following Equation 8:

$$h_i = \Sigma_j M_h(i,j) p_j \quad (8)$$

It should be appreciated that one or more of the above terms may be eliminated and/or omitted for certain plant types, while other or different terms related to other factors may be added or included. For example, the probability of success of the heterotic group may be omitted from the above selection algorithm for selection for soybeans and other varietal crops/plants.

In connection with the term $o_i$, the term $M_l$ included therein (see Equation 6) is an incidence matrix representative of the group of progenies relative to different origins, where the presence of the origin is a "1" and the absence of the origin is a "0." A simplified example matrix is illustrated below in Table 3, as related to the progenies illustrated in FIG. 4. In particular in this exemplary embodiment, $M_l$ is the transpose of the matrix shown in Table 3.

TABLE 3

|                  | $A_1 \times A_2$ | $A_1 \times A_4$ |
|------------------|------------------|------------------|
| $A_1 \times A_2$@0001 | 1                | 0                |
| $A_1 \times A_2$@0002 | 1                | 0                |
| $A_1 \times A_4$@0001 | 0                | 1                |
| $A_1 \times A_4$@0002 | 0                | 1                |
| ...              | ...              | ...              |

In connection with the term $b_i$, the term $M_O$ included therein (see Equation 7) is an incidence matrix from a set of origins to a set of pedigrees. This is similar to the matrix above related to the origins. One simplified example of $M_O$ is presented in Table 4. In particular in this example, $M_o$ is the transpose of the matrix shown in Table 4.

TABLE 4

|                  | $A_1$ | $A_2$ | $A_3$ | $A_4$ |
|------------------|-------|-------|-------|-------|
| $A_1 \times A_2$@0001 | 1     | 1     | 0     | 0     |
| $A_1 \times A_2$@0002 | 1     | 1     | 0     | 0     |
| $A_1 \times A_4$@0001 | 1     | 0     | 0     | 1     |
| $A_1 \times A_4$@0002 | 1     | 0     | 0     | 1     |
| ...              | ...   | ...   | ...   | ...   |

Further in the above equations, the term $\chi_M$ is a characteristics vector for male progenies. The term $\chi_F$ is a characteristics vector for female progenies. The term $M_{T_k}$ is an incidence matrix from progenies for trait $T_k$. That is, it is a matrix, which is indicative of the presence of an absence of a trait in the progeny, based on one or more thresholds. Further, the terms $\alpha_{T_k}^l$, $\alpha_{T_k}^h$ are lower and upper portfolio bounds for trait $T_k$. The term $M_H$ is an incidence matrix from progenies to heterotic groups. Like above, this matrix includes the group of progenies relative to the inclusion of the progenies in the heterotic group. And, the terms are each weights corresponding to various objectives. For example, $\lambda_p$ is the value to be used to weight the performance, $\lambda_r$ is the value to be used to weight the risk, and $\lambda_d$ is the value to be used for diversifying various different factors like origins, lines, heterotic groups, etc.

What's more, the following Equation 9 provides that the total number of progenies identified to the set of progenies equals r.

$$\Sigma_{i=1}^{nN} x_i = r \quad (9)$$

In addition, the set identification algorithm (Equation 2) may further be restricted by Equations 10-12, which identify feasible ones of the filtered group of progenies that may be included in the set of identified progenies. Specifically, Equation 10 limits the male participation in the set of progenies, while Equation 11 limits the female participation in the set of progenies. By their inclusion, Equations 10 and 11 restrict and/or guarantee gender balance in the selected progenies (as desired). Specifically, Equations 10 and 11 guarantee the gender balance in the selected progenies. And, $X_F$ and $X_M$ are the characteristic vectors of female and male gender. For instance, $X_F$ is "1" for all female lines, and "0" for male lines. It can be observed that $X_M(i)+X_F (0=1$. Further, $\alpha_F$ and $\alpha_m$ are a limit of the proportions (e.g., minimum proportions of female and male lines, etc.) to be present in the selected progenies to the set of progenies.

$$\Sigma_{i=1}^{nN} X_M(i) * x_i \geq \alpha_M \cdot r \quad (10)$$

$$\Sigma_{i=1}^{nN} X_F(i) * x_i \geq \alpha_F \cdot r \quad (11)$$

Moreover, Equation (3) identifies ones of the progenies based on the presence of one or more traits, where the matrix M indicates the presence or absence of a trait based on, for example, the phenotypic data associated with the progeny and/or origins from which the progeny is provided, relative to one or more thresholds. The matrix, in this example, includes "1" for trait present and "0" for trait not present.

As used in this exemplary embodiment, the term $T_k$ provides a trait for which is to be included in the set of progenies, such that the term does not give rise to a deviation or cos in Equation (2), but must be followed in this example. And, $\alpha_{T_k}^l(i)$ and $\alpha_{T_k}^u(i)$ are allowable lower and upper bounds, which may be based, for example, on one or more business and/or commercial strategies (or analytics based on need and/or historical data). For instance, if $T_k$ is representative of a certain disease trait then, $\alpha_{T_k}^u(i)$ could be the maximum permissible number of lines in the selections which could have some risk of disease susceptibility. The term $\alpha_{T_k}^l(i)$, for this particular example, would be 0. Another example could be $T_k$ is whether the relative maturity of a plant is within a range. As such, upper and lower limits may be employed to ensure and/or provide that the number of lines to be selected by the set identification algorithm is within a desired bound for that relative maturity group (or one or more other trait(s) as necessary or desired), etc. In this exemplary embodiment, Equation 12 is a strict constraint in connection with step 310, as it must be followed in identifying the set of progenies. Equation 12 may be modified, revised and/or altered in other embodiments (in connection with Equation 2, for example) to provide a cost and/or penalty, in the identification of the set of progeny, consistent with Equations 13-15 below.

$$\alpha_{T_k}^l(i) \leq \Sigma_{j=1}^N M_{T_k}(i,j)^* x_j \leq \alpha_{T_k}^h(i) \tag{12}$$

In addition, and as generally noted above, the set identification algorithm (Equation 2) includes terms directed to a performance profile for the origins, the pedigree, and the family, as provided in and/or account for by Equations 13-15 below. Specifically, Equation 13 accounts for a performance profile for the origins of the progenies, $o_i$, which is defined above, determines a deviation between the set of progenies within the group of progenies, and then bounds that deviation between $-\theta_i$ and $\theta_i$. The deviation from the origin is then a penalty or reduction in the set identification algorithm. Likewise, Equations 14 and 15 are employed, with a performance profile for pedigree and family of the progeny, respectively, whereby deviations, again, are penalties or reductions (e.g., costs, etc.) in the set identification algorithm (Equation 2) above.

$$-\theta_i \leq (\Sigma_{j=1}^{nN} M_I(i,j)^* x_j) - o_i \leq \theta_i \tag{13}$$

$$-\varphi_k \leq \Sigma_{j=1}^N M_o(k,j)(\Sigma_{j=1}^{nN} M_I(i,j)^* x_j) - b_k \leq \varphi_k \tag{14}$$

$$-\gamma_i \leq \Sigma_{j=1}^{nN} M_H(i,j)^* x_j - h_j \leq \gamma_i \tag{15}$$

In this exemplary embodiment, as should be understood, $\theta_i$, $\varphi_k$, $\gamma_i$ are three auxiliary variables, which are introduced to ensure that the diversity profiles are maintained, in other words, that all the selections do not come from the same origin, pedigree, or heterotic groups.

While Equations 13-15 include penalties associated with deviation from a profile, specific to origins, pedigrees, and family, one or more of these penalties, whether represented by the above equations, or other equations, may be omitted from other set identification algorithms. Specifically, the performance term/indicator may be used alone to identify progenies to the set, and/or the performance term/indicator may be used only in combination with the risk function (or other suitable functions).

Finally in the method 300, from the above determinations, the selection engine 110 identifies, at 310, the r number of progenies to include in the set of progenies for advancement. And, the selection engine 110 then directs, at 312, the set of progeny to further iterations of the cultivation and testing phase 106 and/or to the validation phase 108, thereby advancing the identified set of progenies toward commercial activities. For example, one or more plants, which are derived from the identified set of progenies (e.g., one or more plants per identified progeny, etc.), is included (e.g., planted, etc.) in a growing space (e.g., greenhouses, shade houses, nurseries, breeding plots, fields (or test fields), etc.) in the breeding pipeline 102, as part of the cultivation and testing phase 106 or the validation phase 108. The plant(s) in the growing space(s) are grown and/or otherwise subjected to testing and/or commercial activities. In addition, the identification of the set of progenies and/or the advancement thereof is included in the data structure 112, thereby providing feedback into the methods for continued improved performance in subsequent iterations, cycles, season, etc.

It should be appreciated that prior to reliance on any particular method or combination of methods, the selection engine 110 may evaluate performance of the method(s) and select, if necessary, the one that provides the best prediction for a given crop and/or a given region, for example. In order to evaluate the performance of the methods and/or models, historical data may be collected and then partitioned into training and test sets for each of the methods. Models are then built, based on the different methods, using the training data to predict the commercial success using several features for various traits, and using the historical advancement/success of the parents of the progeny. Once the models are built, the commercial success of the test data is predicted through the models and compared to the actual commercial success for the progeny, to determine the accuracy of the models (e.g., for each of the different methods, etc.). With that in mind, it should be appreciated that the models, algorithms, equations, etc. included herein are exemplary in nature, and not limiting to the present disclosure (as other models, algorithms, equations, etc. may be used in other implementations of the system 100 and/or the method 300).

In view of the above, the methods and systems herein permit the identification of progenies to be advanced in a breeding pipeline. Specifically, in a commercial breeding pipeline, the number of potential origins and the number of potential progenies from the origins is substantially reduced, as demonstrated above. In addition, by utilizing a selection engine, which is subject to the algorithms and/or executable instructions described herein, the methods and systems provide for the selection of the set of progenies, which are predicted to be high performing progenies, relative to other progenies in given pools and/or groups of progenies not selected, while consuming minimal resources (or at least reducing the resources consumed).

In this manner, a role of the breeder's expectations, tendencies and/or assumptions is reduced in the process, resulting in a more efficient capture of commercially viable progeny from the universe of potential progeny. Through the systems and methods disclosed herein, breeders can vastly improve the associated breeding pipelines to identify and potentially select those progeny for advancement based on analysis of a universe of data related to the progenies, where, by comparison, in the past conventional breeding methods were limited in what could be considered and how it could be considered. Furthermore, the methods and systems herein are not limited geographically, or otherwise, in any way. For example, if a crop can be grown in a given area, the selection engine 110 herein can be used to identify a set of progeny for that specific market/environment by weighting the data corresponding to certain traits that affect crop performance and/or success in that environment. Such environments may be represented globally or regionally, or they may be as granular as a specific location within a field (such that the same field is identified to have different environments). In this way, the methods and systems herein may be used to target the development of products specific to certain markets, geographies, soil types, etc., or with directives to maximize profits, maximize customer satisfaction, minimize production costs, etc.

With that said, it should be appreciated that the functions described herein, in some embodiments, may be described in computer executable instructions stored on a computer readable media, and executable by one or more processors. The computer readable media is a non-transitory computer readable media. By way of example, and not limitation, such computer readable media can include RAM, ROM, EEPROM, CD-ROM or other optical disk storage, magnetic disk storage or other magnetic storage device, or any other medium that can be used to carry or store desired program code in the form of instructions or data structures and that can be accessed by a computer. Combinations of the above should also be included within the scope of computer-readable media.

It should also be appreciated that one or more aspects of the present disclosure transform a general-purpose computing device into a special-purpose computing device when configured to perform the functions, methods, and/or processes described herein.

As will be appreciated based on the foregoing specification, the above-described embodiments of the disclosure may be implemented using computer programming or engineering techniques, including computer software, firmware, hardware or any combination or subset thereof, wherein the technical effect may be achieved by performing at least one of the following operations: (a) accessing a data structure including data representative of a pool of progenies; (b) determining, by at least one computing device, a prediction score for at least a portion of the pool of progenies based on the data included in the data structure, the prediction score indicative of a probability of selection of the progeny based on historical data; (c) selecting, by the at least one computing device, a group of progenies from the pool of progenies based on the prediction score; (d) identifying, by the at least one computing device, a set of progenies, from the group of progenies, based on at least one of an expected performance of the group of progenies, risks associated with ones of the group of progenies and a deviation of the group of progenies from at least one profile; and (e) directing the set of progenies to a testing and cultivation phase of a breeding pipeline and/or to a validation phase of the breeding pipeline.

Examples and embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. In addition, advantages and improvements that may be achieved with one or more exemplary embodiments disclosed herein may provide all or none of the above mentioned advantages and improvements and still fall within the scope of the present disclosure.

Specific values disclosed herein are example in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may also be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When a feature is referred to as being "on," "engaged to," "connected to," "coupled to," "associated with," "in communication with," or "included with" another element or layer, it may be directly on, engaged, connected or coupled to, or associated or in communication or included with the other feature, or intervening features may be present. As used herein, the term "and/or" includes any and all combinations of one or more of the associated listed items.

Although the terms first, second, third, etc. may be used herein to describe various features, these features should not be limited by these terms. These terms may be only used to distinguish one feature from another. Terms such as "first," "second," and other numerical terms when used herein do not imply a sequence or order unless clearly indicated by the context. Thus, a first feature discussed herein could be termed a second feature without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for identifying progeny for use in a plant breeding pipeline, the method comprising:
   accessing a data structure including data representative of a pool of progenies;
   determining, by at least one computing device, a prediction score for at least a portion of the pool of progenies based on the data included in the data structure, the prediction score indicative of a probability of selection of the progeny based on historical selection data for the pool of progenies;

selecting, by the at least one computing device, a group of progenies from the pool of progenies based on the prediction score;

identifying, by the at least one computing device, a set of progenies from the group of progenies based on at least one of: an expected performance of the set of progenies and at least one factor associated with the set of progenies, the pool of progenies and/or the group of progenies;

wherein the at least one factor includes one or more of: risk, genetic diversity, trait(s) of the set of progenies, probability of success of base origins, probability of success of base pedigrees, and/or probability of success of heterotic groups; and directing the set of progenies to a testing and cultivation phase of the plant breeding pipeline and/or to a validation phase of the breeding pipeline.

2. The method of claim 1, further comprising generating, by the at least one computing device, a prediction model based on historical phenotypic data included in the data structure, the historical phenotypic data associated with plant material of a type consistent with a plant type of the pool of progenies; and wherein determining the prediction score includes determining the prediction score based on the prediction model.

3. The method of claim 1, wherein the data includes phenotypic data representative of the pool of progenies; and wherein selecting the group of progenies includes selecting one or more progenies from the pool when the prediction score of the selected progeny satisfies one or more thresholds.

4. The method of claim 1, wherein identifying the set of progenies is based on the following set identification algorithm:

$$x_{opt} = \underset{x \in \{0,1\}^{nN}}{\mathrm{argmax}} \left( \lambda_p \sum_{i=1}^{nN} x_i p_i - \lambda_r \sum_{i=1}^{nN} x_i r_i - \lambda_{d_1} 1^T \theta - \lambda_{d_2} 1^T \varphi - \lambda_{d_3} 1^T \gamma \right);$$

wherein $\lambda_p \Sigma_{i=1}^{nN} x_i p_i$ is associated with performance of the group of progenies; $\lambda_r \Sigma_{i=3}^{nN} x_i r_i$ is associated with risk; $\lambda_{d_1} 1^T \theta$, $\lambda_{d_2} 1^T \varphi$, and $\lambda_{d_3} 1^T \gamma$ are associated with deviations from one or more performance profiles; and $p_i$, and $r_i$ are associated with performance and risk scores, respectively, for the group of progenies.

5. The method of claim 4, wherein the set identification algorithm is subject to at least one of the following algorithms:

$$\sum_{i=1}^{nN} X_M(i) * x_i \geq \alpha_M \cdot r;$$

$$\sum_{i=1}^{nN} X_F(i) * x_i \geq \alpha_F \cdot r; \text{ and}$$

$$\alpha^l_{T_k}(i) \leq \sum_{j=1}^{N} M_{T_k}(i,j) * x_j \leq \alpha^h_{T_k}(i);$$

wherein $X_F$ and $X_M$ are vectors of female and male gender of the group of progenies; $T_k$ is a trait to be included in the group of progenies; matrix M indicates the presence or absence of said trait in the group of progenies; and $\alpha_{T_k}^l(i)$ and $\alpha_{T_k}^u(i)$ are lower and upper bounds, respectively.

6. The method of claim 5, wherein the set identification algorithm is subject to at least one of the following algorithms:

$$-\theta_i \leq \sum_{j=1}^{nN} M_I(i,j) * x_j - o_j \leq \theta_i;$$

$$-\varphi_k \leq \sum_{j=1}^{N} M_o(k,j) \left( \sum_{j=1}^{nN} M_I(i,j) * x_j \right) - b_k \leq \varphi_k; \text{ and}$$

$$-\gamma_i \leq \sum_{j=1}^{nN} M_H(i,j) * x_j - h_j \leq \gamma_i;$$

wherein $\theta_i$, $\varphi_k$, $\gamma_i$ include auxiliary variables; $o_i$ is a performance profile for origins of said group of progenies; $-\theta_i$ and $\theta_i$ are bounds of a deviation defined by $o_i$.

7. The method of claim 1, wherein directing the set of progenies to a testing and cultivation phase of a breeding pipeline includes including one or more plants in a growing space of the breeding pipeline, the one or more plants derived from the identified set of progenies.

8. A system for identifying progeny for use in plant breeding, the system comprising:

a data storage device including phenotypic data related to a pool of progenies, each of the progenies based on one or more origins; and a computing device coupled in communication with the data storage device and configured, by executable instructions, to:

access the phenotypic data in the data structure related to the pool of progenies;

determine a prediction score for each of the progenies in the pool of progenies based on the accessed phenotypic data, the prediction score indicative of a probability of selection of the progeny based on historical selection data for the pool of progenies;

select a group of progenies from the pool of progenies based on the prediction score for each of the progenies in the pool of progenies;

identify a set of progenies, from the group of progenies, based on at least two of: expected performance of the progenies, a risk associated with the set of progenies, and a deviation of the set of progenies from at least one desired profile, wherein the expected performance of the set of progenies includes a probability of success of the progenies; and direct the set of progenies to a validation phase for planting and/or testing and/or to a validation phase of a breeding pipeline for commercialization.

9. The system of claim 8, wherein the computing device is further configured to identify the set of progenies based on the following algorithm:

$$x_{opt} = \underset{x \in \{0,1\}^{nN}}{\mathrm{argmax}} \left( \lambda_p \sum_{i=1}^{nN} x_i p_i - \lambda_r \sum_{i=1}^{nN} x_i r_i - \lambda_{d_1} 1^T \theta - \lambda_{d_2} 1^T \varphi - \lambda_{d_3} 1^T \gamma \right);$$

wherein $\lambda_p \Sigma_{i=1}^{nN} x_i p_i$ is associated with performance of the group of progenies; $\lambda_r \Sigma_{i=3}^{nN} x_i r_i$ is associated with risk; $\lambda_{d_1} 1^T \theta$, $\lambda_{d_2} 1^T \varphi$, and $\lambda_{d_3} 1^T \gamma$ are associated with deviations from one or more performance profiles; and $p_i$, and $r_i$ are associated with performance and risk scores, respectively, for the group of progenies.

10. The system of claim 8, further comprising the breeding pipeline coupled in communication with the computing device, the breeding pipeline including the cultivation and testing phase and the validation phase;
    wherein the computing device is configured to gather at least a portion of the phenotypic data included in the data structure and to store the at least a portion of the phenotypic data included in the data structure; and
    wherein a plant derived from at least one of the set of progenies is planted in a growing space of the validation phase of the breeding pipeline, after the set of progenies are directed to the breeding pipeline.

11. The system of claim 8, wherein the computing device is further configured to identify, based on a user input, the pool of progenies, prior to accessing the phenotypic data in the data structure related to the pool of progenies.

12. The system of claim 8, wherein the computing device is configured to identify the set of progenies based on a value associated with the probability of success of the set of progenies less a value associated with a deviation of the set of progenies from a desired profile.

13. The system of claim 8, further comprising a growing space of the breeding pipeline; and
    wherein the growing space includes at least one plant included in the growing space, the at least one plant derived from at least one of the progenies of the identified set of progenies.

14. A non-transitory computer readable storage media including executable instructions for identifying progeny for use in plant breeding, which, when executed by at least one processor, cause the at least one processor to:
    access a data structure including data representative of a pool of progenies;
    determine a prediction score for at least a portion of the pool of progenies based on the data included in the data structure, the prediction score indicative of a probability of selection of the progeny based on historical selection data for the pool of progenies;
    select a group of progenies from the pool of progenies based on the prediction score;
    identify a set of progenies, from the group of progenies, based on: an expected performance of the set of progenies and/or at least one factor associated with the pool of progenies, the group of progenies, and/or the set of progenies, a probability of success associated with base origins of the set of progenies, a probability of success associated with base pedigrees of the set of progenies, and a probability of success associated with the heterotic groups of the set of progenies; and
    direct the set of progenies to a testing and cultivation phase of a breeding pipeline and/or to a validation phase of the breeding pipeline.

15. The non-transitory computer readable storage media of claim 14, wherein the executable instructions, when executed by the at least one processor, further cause the at least one processor to generate a prediction model based on historical phenotypic data included in the data structure, the historical phenotypic data associated with plant material of a type consistent with a plant type of the pool of progenies; and/or
    wherein the executable instructions, when executed by the at least one processor in connection with determining the prediction score, cause the at least one processor to determine the prediction score based on the prediction model.

16. The non-transitory computer readable storage media of claim 15, wherein the data includes phenotypic data representative of the pool of progenies; and/or
    wherein the executable instructions, when executed by the at least one processor in connection with selecting the group of progenies, cause the at least one processor to select one or more progenies from the pool when the prediction score of the selected progeny satisfies one or more thresholds.

17. The non-transitory computer readable storage media of claim 15, wherein the executable instructions, when executed by the at least one processor in connection with identifying the set of progeny, cause the at least one processor to identify the set of progeny based on the following set identification algorithm:

$$x_{opt} = \underset{x \in \{0,1\}^{nN}}{\arg\max} \left( \lambda_p \sum_{i=1}^{nN} x_i p_i - \lambda_r \sum_{i=1}^{nN} x_i r_i - \lambda_{d_1} 1^T \theta - \lambda_{d_2} 1^T \varphi - \lambda_{d_3} 1^T \gamma \right);$$

wherein the set identification algorithm is subject to at least one of the following algorithms:

$$\sum_{i=1}^{nN} X_M(i) * x_i \geq \alpha_M \cdot r;$$

$$\sum_{i=1}^{nN} X_F(i) * x_i \geq \alpha_F \cdot r;$$

$$\alpha_{T_k}^l(i) \leq \sum_{j=1}^{N} M_{T_k}(i,j) * x_j \leq \alpha_{T_k}^h(i);$$

$$-\theta_i \leq \sum_{j=1}^{nN} M_l(i,j) * x_j - o_j \leq \theta_i;$$

$$-\varphi_k \leq \sum_{j=1}^{N} M_o(k,j) \left( \sum_{j=1}^{nN} M_l(i,j) * x_j \right) - b_k \leq \varphi_k; \text{ and}$$

$$-\gamma_i \leq \sum_{j=1}^{nN} M_H(i,j) * x_j - h_j \leq \gamma_i;$$

wherein $\lambda_p \Sigma_{i=1}^{nN} x_i p_i$ is associated with performance of the group of progenies; $\lambda_r \Sigma_{i=3}^{nN} x_i r_i$ is associated with risk; $\lambda_{d_1} 1^T \theta$, $\lambda_{d_2} 1^T \varphi$, and $\lambda_{d_3} 1^T \gamma$ are associated with deviations from one or more performance profiles; and $p_i$, and $r_i$ are associated with performance and risk scores, respectively, for the group of progenies;
wherein $X_F$ and $X_M$ are vectors of female and male gender of the group of progenies; $T_k$ is a trait to be included in the group of progenies; matrix M indicates the presence or absence of said trait in the group of progenies; and $\alpha_{T_k}^l(i)$ and $\alpha_{T_k}^u(i)$ are lower and upper bounds, respectively; and
wherein $\theta_i$, $\varphi_k$, $\gamma_i$ include auxiliary variables; $o_i$ is a performance profile for origins of said group of progenies; $-\theta_i$ and $\theta_i$ are bounds of a deviation defined by $o_i$.

18. The non-transitory computer readable storage media of claim 15, wherein the at least one factor includes at least one of: a risk associated with the set of progenies, a deviation of the set of progenies from at least one profile, risk, genetic diversity, one or more traits of the set of progenies, probability of success of base origins, probability of success of base pedigrees, probability of success of heterotic groups, one or more trait profiles, market segmentation, production cost, and/or trait integration.

* * * * *